(12) United States Patent
Bergmann

(10) Patent No.: US 7,659,075 B2
(45) Date of Patent: *Feb. 9, 2010

(54) METHOD FOR THE DIAGNOSIS OF SEPSIS WITH DETERMINATION OF SOLUBLE CYTOKERATIN FRAGMENTS

(75) Inventor: Andreas Bergmann, Berlin (DE)

(73) Assignee: B.R.A.H.M.S Aktiengesellschaft, Hennigsdorf (DE)

( * ) Notice: Subject to any disclaimer, the term of this patent is extended or adjusted under 35 U.S.C. 154(b) by 185 days.

This patent is subject to a terminal disclaimer.

(21) Appl. No.: 10/496,096

(22) PCT Filed: Nov. 29, 2002

(86) PCT No.: PCT/EP02/13526

§ 371 (c)(1),
(2), (4) Date: Dec. 22, 2004

(87) PCT Pub. No.: WO03/048782

PCT Pub. Date: Jun. 12, 2003

(65) Prior Publication Data
US 2005/0106645 A1    May 19, 2005

(30) Foreign Application Priority Data
Dec. 4, 2001  (EP) .................................. 01128851

(51) Int. Cl.
*G01N 33/53* (2006.01)
(52) U.S. Cl. ......................................... 435/7.1; 436/811
(58) Field of Classification Search ....................... None
See application file for complete search history.

(56) References Cited

U.S. PATENT DOCUMENTS

| | | | |
|---|---|---|---|
| 5,639,617 A | 6/1997 | Bohuon | 435/7.1 |
| 5,660,994 A | 8/1997 | Bruder-Heid et al. | 435/7.23 |
| 6,207,380 B1 * | 3/2001 | Billing-Medel et al. | 435/6 |
| 7,132,246 B2 * | 11/2006 | Bergmann et al. | 435/7.1 |
| 7,157,081 B2 * | 1/2007 | Bergmann et al. | 424/94.1 |
| 7,405,049 B2 | 7/2008 | Bergmann et al. | |
| 7,413,850 B2 | 8/2008 | Bergmann et al. | |
| 2002/0103141 A1 * | 8/2002 | McKearn et al. | 514/43 |
| 2004/0002125 A1 * | 1/2004 | Gombrich et al. | 435/7.23 |
| 2005/0059104 A1 | 3/2005 | Bergmann et al. | |
| 2005/0064506 A1 | 3/2005 | Bergmann et al. | |
| 2005/0239150 A1 | 10/2005 | Bergmann et al. | |
| 2006/0029990 A1 | 2/2006 | Bergmann et al. | |
| 2006/0035221 A1 | 2/2006 | Bergmann et al. | |
| 2006/0115869 A1 | 6/2006 | Bergmann et al. | |
| 2006/0234295 A1 | 10/2006 | Bergmann et al. | |

FOREIGN PATENT DOCUMENTS

| | | |
|---|---|---|
| DE | 198 47 690 A1 | 4/2000 |
| DE | 101 19 804 A1 | 10/2002 |
| DE | 101 30 985 A1 | 1/2003 |
| DE | 101 31 922 A1 | 1/2003 |
| EP | 1 318 405 B1 | 11/2004 |
| WO | WO 00/22439 | 4/2000 |
| WO | WO 02/085937 A2 | 10/2002 |
| WO | WO 03/002600 A1 | 1/2003 |
| WO | WO 03/005035 A1 | 1/2003 |

OTHER PUBLICATIONS

Vogl et al. Clinical Biochemistry vol. 28 (1995), pp. 291-295.*
Mayeux et al. "Biomarkers: Potential uses and Limitations"; NeuroRx (2004); vol. 1, pp. 182-188.*
Dobashi et al. "Elevated serum and BAL cytokeratin 19 fragment in pulmonary fibrosis and acute interstitial pneumonia" Eur Respir J 1999; 14: 574-578.*
Tempfer et al. "CYFRA 21-1 serum levels in women with adnexal masses and inflammatory diseases" Br J Cancer. Oct. 1998;78(8):1108-12; abstract only.*
Bast et al. "Translational Crossroads for Biomarkers" Clin Cancer Res 2005; 11(17), 6103-6108.*
LaBaer et al. "So, You Want to Look for Biomarkers" Journal of Proteome Research 2005; 4, 1053-1059.*
Baker "In Biomarkers We Trust?" Nature Biotechnology 2005; 23(3), 297-304.*
Harlow, E. and Lane, D., Antibodies: A Laboratory Manual (1988) Cold Spring Harbor Laboratory Press, Cold Spring Harbor, NY, pp. 23-25.*
Williams, M.D. et al. "Hospitalized cancer patients with severe sepsis: analysis of incidence, mortality, and associated costs of care" Critical Care 2004, 8:R291-R298 (DOI 10.1186/cc2893.*
Advisory Action dated Oct. 14, 2008 in co-pending U.S. Appl. No. 10/496,096; RCE filed Nov. 24, 2008.
Office Action dated Nov. 13, 2008 in co-pending U.S. Appl. No. 10/496,250.
Final Rejection dated Oct. 14, 2008 in co-pending U.S. Appl. No. 10/497,679.
Final Rejection dated Oct. 31, 2008 in co-pending U.S. Appl. No. 10/516,618.
Office Action dated Jul. 9, 2008 in co-pending U.S. Appl. No. 10/496,173.
Aird, "The Hematologic System as a Marker of Organ Dysfunction in Sepsis," *Mayo Clin, Proc.*, 78:869-881, 2003.
Assicot, et al., "High Serum Procalcitonin Concentrations in Patients with Sepsis and Infection," *Lancet*, 341(8844):515-518, 1993.

(Continued)

*Primary Examiner*—Christopher L Chin
*Assistant Examiner*—Christine Foster
(74) *Attorney, Agent, or Firm*—Heslin Rothenberg Farley & Mesiti P.C.

(57) ABSTRACT

Method for early differential diagnosis and detection, for prognosis and assessment of the severity and for therapy-accompanying assessment of the course of sepsis and sepsis-like systemic infections, in which, preferably with additional determination of at least one further parameter suitable for sepsis diagnosis, the amount of soluble cytokeratin fragments, in particular of CYFRA 21-1, TPS, TPA and/or sCY1F, in a biological fluid of a patient in whom a sepsis is present or a sepsis is suspected is determined and conclusions with regard to the presence, the expected course, the severity and/or the success of initiated measures for the therapy of the sepsis are drawn from the determined amount of soluble cytokeratin fragments.

4 Claims, 4 Drawing Sheets

OTHER PUBLICATIONS

Beishuizen et al, "Endogenous Mediators in Sepsis and Septic Shock," *Advances Clin. Chem.*, 33:55-131, 1999.

Carrigan et al., "Toward Resolving the Challenges of Sepsis Diagnosis," *Clin. Chem.*, 50(8):1301-1314, 2004.

Ebert et al., "CYFRA 21-1—Clinical Applications and Analytical Requirements," *Scand J. Clin. Lab. Invest.*, 55 Suppl. 221:72-80, 1995.

Einarsson and Rydlander, "Tissue Polypeptide Specific Antigen (TPS) Detects a Specific Epitope Structure on Human Cytokeratin," *Anticancer Research*, 17:3121-3124, 1997.

Gabay and Kushner, "Acute-Phase Proteins and Other Systemic Responses to Inflammation," *New Engl. J. Med.*, 340(6):448-454, 1999.

Hotchkiss and Karl, "The Pathophysiology and Treatment of Sepsis," *N. Engl. J. Med.*, 348(2):138-150, 2003.

Karzai, et al., "Procalcitonin—A New Indicator of the Systemic Response to Severe Infections," *Infection*, 25:3-8, 1997.

Kim et al., "Different Cutoff Values of Cyfra 21-1 for Cavitary and Noncavitary Lung Cancers," *Lung Cancer*, 30:187-192, 2000.

Marshall et al., "Measures, Markers, and Mediators: Toward a Staging System for Clinical Sepsis. A Report of the Fifth Toronto Sepsis Roundtable, Toronto, Ontario, Canada, Oct. 25-26, 2000," *Crit. Care Med.*, 31(5):1560-1567, 2003 (Abstract only).

Nisman et al., "Evaluation of Tissue Polypeptide Specific Antigen, CYFRA 21-1, and Carcinoembryonic Antigen in Nonsmall Cell Lung Carcinoma," *Cancer*, 82:1850-1859, 1998.

Oberholzer et al., "Sepsis Syndromes: Understanding the Role of Innate and Acquired Immunity," *Shock*, 16(2):83-96, 2001 (Abstract only).

Oczenski et al., "Procalcitonin: A New Parameter for the Diagnosis of Bacterial Infection in the Peri-Operative Period," *Eur. J. Anaesthesiol.*, 15:202-209, 1998.

Redl et al., "Procalcitonin Release Patterns in a Baboon Model of Trauma and Sepsis: Relationship to Cytokines and Neopterin," *Crit. Care Med.*, 28(11):3659-3663, 2000.

Redl and Schlag, "Non-Human Primate Models of Sepsis," *Sepsis*, 2:243-253, 1998.

Reinhart et al., "Sepsis Und Spetischer Schock," *Intensivmedizin*, 756-760, 2001.

Rylander et al., "Molecular Characterization of a Tissue-Polypeptide-Specific-Antigen Epitope and its Relationship to Human Cytokeratin 18," *Eur. J. Biochem.*, 241:309-314, 1996.

Sarwar et al., "CYFRA 21-1 as a Tumor Marker Used in Measuring the Serum Fragment of Cytokeratin Subunit 19 by Immunoradiometric Assay," *Annals of Nucl. Med.*, 8(4), 301-306, 1994.

Stearns et al., "Circulating Tumor Markers in Breast Cancer: Accepted Utilities and Novel Prospects," *Breast Cancer Research Treatment*, 52:239-259, 1998.

Stieber, "34.10 CYFRA 21-1 (Cytokeratin-19-Fragmente)," *Thomas Labor Diagnose*, 987-992, 2000.

Streicher et al., "Anticytokeratins Are a Potential Source of False-Positive Indirect Immunofluorescence Assays for C-ANCA," *J. Clin. Lab. Analys.*, 12:54-59, 1998.

Sutterlin et al., "Clinical Value of CYFRA 8/18 and TPS in the Diagnosis and Follow Up of Invasive Breast Cancer," *Anticancer Research*, 17:2963-2966, 1997.

Trevisani et al., "Cytokeratin Tumor Marker Levels in Bronchial Washing in the Diagnosis of Lung Cancer," *Chest*, 109:104-108, 1996.

Wolff et al., "Tissue Polypeptide Specific Antigen Serum Concentrations in Patients with Newly Diagnosed Prostatic Diseases," *Anticancer Research*, 20:5003-5006, 2000.

Yao et al., "Clinicopathologic Correlation of Serum Tissue Polypeptide Specific Antigen in Hepatocellular Carcinoma," *Oncology*, 61:64-70, 2001.

International Search Report for EPO Application No. 01128851.1, mailed Jun. 4, 2002.

International Search Report for PCT Application No. PCT/EP 02/13526, mailed Nov. 29, 2002.

* cited by examiner

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Contains a
      partial (AA 14 to 29) sequence of cytokeratin 1

-continued

```
<400> SEQUENCE: 1

Cys Leu Gln Gln Val Asp Thr Ser Thr Arg Thr His Asn Leu Glu Pro
  1               5                  10                  15
Tyr
```

METHOD FOR THE DIAGNOSIS OF SEPSIS WITH DETERMINATION OF SOLUBLE CYTOKERATIN FRAGMENTS

The present application is a nationalization of PCT Application Serial No. PCT/EP02/13526, filed Nov. 29, 2002, which claims priority to European application No. 01128851.1, filed Dec. 4, 2001.

BACKGROUND OF THE INVENTION

Field of the Invention

The invention relates to a novel method for sepsis diagnosis, in which or in the course of which soluble cytokeratin fragments are determined.

The invention is based on the detection, for the first time, of greatly increased concentrations of various soluble cytokeratin fragments in the blood circulation of patients in whom a bacterial sepsis had been diagnosed on the basis of clinical findings and simultaneously increased concentrations of the known sepsis marker procalcitonin. Said soluble cytokeratin fragments also include in particular the parameters CYFRA 21-1 and TPS (tissue polypeptide specific antigen) known from other contexts, in particular as tumour markers, and the more unspecific historical precursor thereof TPA (tissue polypeptide antigen).

The present invention has its origin in intensive research work by the Applicant in relation to further improvements of the diagnosis and therapy of inflammations of infectious aetiology and sepsis.

Inflammations are defined very generally as certain physiological reactions of an organism to different types of external effects, such as, for example, injuries, burns, allergens, infections by microorganisms, such as bacteria and fungi and viruses, to foreign tissues which trigger rejection reactions, or to certain inflammatory endogenous conditions of the body, for example in autoimmune diseases and cancer. Inflammations may occur as harmless, localized reactions of the body but are also typical features of numerous serious chronic and acute diseases of individual tissues, organs, organ parts and tissue parts.

In sepsis or septic shock, inflammation-specific reaction cascades spread in an uncontrolled manner over the whole body and may become life-threatening in the context of an excessive systemic immune response. Regarding the current knowledge about the occurrence and possible role of individual groups of endogenous sepsis-specific substances, reference is made, for example, to A. Beishuizen et al., "Endogenous Mediators in Sepsis and Septic Shock", Advances in Clinical Chemistry, Vol. 33, 1999, 55-131; and C. Gabay et al., "Acute Phase Proteins and Other Systemic Responses to Inflammation", The New England Journal of Medicine, Vol. 340, No. 6, 1999, 448-454. Since the understanding of sepsis and related systemic inflammatory diseases, and hence also the recognized definitions, have changed in recent years, reference is also made to K. Reinhart et al., "Sepsis und septischer Schock" [Sepsis and septic shock], in: Intensivmedizin, Georg Thieme Verlag, Stuttgart, New York, 2001, 756-760, where a modern definition of sepsis is given. In the context of the present Application, the term sepsis used is based on the definition as given in the stated references.

Whereas at least in Europe the systemic bacterial infection detectable by a positive blood culture long characterized the term sepsis, sepsis is now primarily understood as being systemic inflammation which is caused by infection. Said transformation in the understanding of sepsis has resulted in changes in the diagnostic approach. Thus, the direct detection of bacterial pathogens was replaced or supplemented by complex monitoring of physiological parameters and, more recently, in particular by the detection of certain substances involved in the sepsis process or in the inflammatory process, i.e. specific "biomarkers".

Of the large number of mediators and acute phase proteins which are known to be involved, or presumed to be involved, in an inflammatory process, the ones which are suitable for purposes of clinical sepsis diagnosis are in particular those which occur with high sensitivity and specificity in sepsis or certain phases of a sepsis or whose concentrations change in a dramatic and diagnostically significant manner and which moreover have the stabilities required for routine determinations and reach high concentration values. For diagnostic purposes, the reliable correlation of pathological process with respective biomarker is of primary importance, without there being any need to know its exact role in the complex cascade of the endogenous substances involved in the inflammatory process.

A known endogenous substance particularly suitable as a sepsis biomarker is procalcitonin. Procalcitonin is a prohormone whose serum concentrations reach very high values under the conditions of a systemic inflammation of infectious aetiology (sepsis), whereas it is virtually undetectable in healthy persons. High values of procalcitonin are also reached in a relatively early stage of a sepsis so that the determination of procalcitonin is also suitable for early diagnosis of a sepsis or for early distinguishing of a sepsis caused by infection from severe inflammations which have other causes. The determination of procalcitonin is furthermore particularly valuable for therapy-accompanying observation of the course of a sepsis. The determination of procalcitonin as a sepsis marker is the subject of the publication by M. Assicot et al., "High serum procalcitonin concentrations in patients with sepsis and infection", The Lancet, Vol. 341, No. 8844, 1993, 515-518; and the patents DE 42 27 454 C2 and EP 0 656 121 B1 and U.S. Pat. No. 5,639,617. Reference is hereby made to said patents and to early literature references mentioned in said publication for supplementing the present description. In recent years, the number of publications on the subject of procalcitonin has greatly increased. Reference is therefore also made to W. Karzai et al., "Procalcitonin—A New Indicator of the Systemic Response to Severe Infection", Infection, Vol. 25, 1997, 329-334; and M. Oczenski et al., "Procalcitonin: a new parameter for the diagnosis of bacterial infection in the peri-operative period", European Journal of Anaesthesiology 1998, 15, 202-209; and furthermore H. Redl et al., "Procalcitonin release patterns in a baboon model of trauma and sepsis: Relationship to cytokines and neopterin", Crit Care Med 2000, Vol. 28, No. 11, 3659-3663; and H. Redl et al., "Non-Human Primate Models of Sepsis", in: Sepsis 1998; 2:243-245; and the further literature references cited therein, as typical of recent published reviews.

The availability of the sepsis marker procalcitonin has given considerable impetus to sepsis research, and intensive efforts are now being made by the Applicant to find further biomarkers which can supplement the procalcitonin determination and/or are capable of providing additional information for purposes of fine diagnosis or differential diagnosis of septic diseases. Attempts are therefore being made in particular to find further biomarkers for sepsis diagnosis, the levels of which in biological fluids, in particular in sera, are regularly increased but which, in their determination, do not simply duplicate the results of the procalcitonin determination but provide additional information, in particular about the stage of the sepsis process, i.e. information preferably to be associated with the course of the sepsis as a function of time, and/or about the initial organ or main organ of a septic process, i.e. localizing information. The aim is finally the selection of a set of sepsis parameters which are simultaneously determined in biological fluids, i.e. in particular in serum, but, for example, also in other biological fluids, such as urine, of sepsis patients or potential sepsis patients, for example with the use of the so-called chip technology or immunochromatographic methods ("point of care" or POC determinations), and in their totality provide an information pattern which clearly surpasses the information value of the determination of only a single parameter.

The search for potential novel sepsis biomarkers is, however, complicated by the fact that frequently very little or nothing is known about the exact function or about the exact reasons for the occurrence of certain endogenous substances which are involved in the inflammation or sepsis process.

Since the endogenous substances present in higher concentration during sepsis are part of the complex reaction cascade of the body, not only are such substances also of diagnostic interest but attempts are also currently being made, with considerable effort, to intervene therapeutically in the sepsis process by influencing the formation and/or the concentration of individual substances of this type, in order, for example, to stop as early as possible the systemic spread of the inflammation, which spread is observed during sepsis. In this context, endogenous substances which have been shown to be involved in the sepsis process are also to be regarded as potential therapeutic targets.

The results of the experimental testing of a fruitful purely hypothetical approach to the determination of further potential sepsis markers are to be found in DE 198 47 690 Al and WO 00/22439. There, it is shown that, in the case of sepsis, not only is the concentration of the prohormone procalcitonin significantly increased but also significantly increased concentrations can be observed for other substances which may be included among the peptide prohormones. The peptide prohormones pro-enkephalin, pro-gastrin-releasing peptide (proGRP), pro-endothelin-1, pro-brain-natriuretic peptide (pro-BNP), pro-atrial-natriuretic peptide (pro-ANP), pro-leptin, pro-neuropeptide-Y, pro-somatostatin, pro-neuropeptide-YY, pro-interleukin-6 or pro-interleukin-10 may be mentioned in this context. While the phenomenon described is well documented, the causes of the increase in the concentrations of prohormones in sepsis are still substantially unexplained.

In the prior unpublished Patent Application DE 101 30 985.6, results of a purely empirical approach are furthermore described, in which, inter alia, a peptide, which was detectable only in the treated animals, was found after an artificial sepsis in liver samples triggered experimentally by toxin administration (LPS from Salmonella Typhimurium) in baboons. It proved to be a soluble cytokeratin-1 fragment (abbreviated below to sCY1F). As shown in the experimental section of this Application, this fragment sCY1F first found in liver extracts of baboons is also found with a sensitivity of 95% in sera of human sepsis patients, whereas it is not detectable in sera of healthy persons.

These experimental findings made it appear worthwhile checking experimentally whether it is possible to measure, in the sera of sepsis patients, also increased concentrations of other soluble cytokeratin fragments, for example of those soluble cytokeratin fragments which already play a role as tumour markers in medical diagnosis.

SUMMARY OF THE INVENTION

Surprisingly, it was found that, in the case of sepsis, some soluble cytokeratin fragments regarded to date as typical tumour markers are significantly increased. This indicates that such fragments are not formed in a tumour-specific manner but tend to indicate a systemic critical physiological process which also affects tissues or organs which release these tumour markers. Although, as shown in this Application and simultaneously filed further Applications, the concentrations of the soluble cytokeratin fragments and of some other tumour markers were increased in the case of sepsis with high sensitivity, there is at the same time no quantitative correlation of the measured values with the likewise significantly increased procalcitonin concentrations, i.e. in individual patients both parameters are found to have increased but in some cases in very different relative amounts.

The term "soluble cytokeratin fragments" is used in the present Application in a comprehensive sense which also includes the soluble cytokeratin-1 fragments disclosed in the prior unpublished Patent Application DE 101 30 985.6. On the basis of the reference made herewith, the content of said prior Patent Application DE 101 30 985.6 is to be regarded as part of the disclosure of the present Application.

To the extent that the disclosure in the prior Application is to be considered as prior art anticipating said term "soluble cytokeratin fragments" and the claimed uses of such fragments, such a disclosure is to be excluded by disclaimer from the scope of the Patent Claims of the present Application.

The present invention is based on the discovery for the first time that significantly increased physiological concentrations of soluble cytokeratin fragments are found in biological fluids, in particular in sera, of sepsis patients, which makes said fragments suitable, in particular in combination with the determination of further sepsis parameters, for the diagnosis of sepsis.

The method according to the invention and certain preferred embodiments thereof are defined more exactly in Claims 1 to 10.

It was not known to date that the concentrations of soluble cytokeratin fragments in biological fluids, in particular in sera, are significantly increased during sepsis and that a determination of the concentration of soluble cytokeratin fragments can therefore also be important for the diagnosis of sepsis. This is true in spite of the fact that some soluble cytokeratin fragments, in particular in the form of the parameter CYFRA 21-1 and of the parameter TPS or of its less specific precursor TPA, are already determined in the course of tumour diagnosis and assays suitable for the determination of these parameters are commercially available.

Because of the present invention, it is possible to use the determination of soluble cytokeratin fragments also in the course of a diagnostic sepsis detection method. Of particular interest is the suitability of soluble cytokeratin fragments as prognosis markers and markers for monitoring the course of sepsis, in particular as part of a combination of measurement with other markers. Owing to the high sensitivity and specificity, soluble cytokeratin fragments, individually or in a combination of different types, are also suitable as markers which can be determined in the course of an initial sepsis diagnosis.

In addition to a combination with a procalcitonin measurement, in particular a combination of the measurement of one or more soluble cytokeratin fragment(s) with the determination of other markers for sepsis and systemic inflammations, which have been regarded to date as typical tumour markers, is suitable, in particular with CA 19-9, CA 125, S100B, or S100A proteins involved in inflammation regulation, or with the determination of the novel sepsis marker inflammin described in the prior, below-mentioned unpublished German Patent Applications of the Applicant (DE 101 19 804.3) and CHP (DE 101 31 922.3) and/or of one or more of the above-mentioned prohormones. A simultaneous determination of the known inflammation parameter C-reactive protein (CRP) may also be envisaged. On the basis of the novel results described in this Application and in the parallel applications, a combination with measurements of known biomolecules or biomolecules still to be discovered should also generally be considered for the fine diagnosis of sepsis, which biomolecules are suitable as tissue- or organ-specific inflammation markers.

The content of said prior Applications of the Applicant is to be considered as part of the disclosure of the present Application by express reference to these Applications.

CYFRA 21-1 is defined as a soluble fragment of cytokeratin 19. Although cytokeratin 19 can be regarded neither as an organ-specific protein nor as a tumour-specific protein, determination of CYFRA 21-1 plays an important role as a tumour marker in the diagnosis, therapy control and monitoring of in particular bronchial carcinoma and for the monitoring of carcinoma of the bladder (cf. Lothar Thomas (editor) : Labor und Diagnose, Section 34.10, pages 987-992, 5th Edition, 1998, TH-Books Verlagsgesellschaft).

In addition to the discoveries to date, CYFRA 21-1 may also be present at increased levels in some nonmalignant diseases, although values of >10 ng/ml are consistent with a benign disease only in extremely rare cases. In benign diseases, the highest values were measured in cases of gastrointestinal diseases. For the measurement of CYFRA 21-1 and for the interpretation of the results of the measurements, reference may be made, in addition to Thomas, loc cit, and the sources mentioned therein, for example, to M. Sawar et al., Ann Nucl Med Vol. 8, No. 4, 301-306, 1994; W. Ebert et al., Scand J Clin Invest 1995; 55 Suppl 221:72-80; Young-Chul Kim et al., Lung Cancer 30 (2000) 187-192.

TPS (tissue polypeptide specific antigen) is defined as a cytokeratin-18 fragment which is related to the so-called TPA (tissue polypeptide antigen) known for more than 40 years, but is better characterized and more specific. In this context, reference may be made to Lars Rylander et al., Eur. J. Biochem. 241, 309-314 (1996); and R. Einarsson et al., Anticancer Research 17:3121-3124 (1997). An antibody M3 which can be used for its determination binds to the amino acids 322-340 of the carboxy-terminated segment of cytokeratin-18. The suitability and use of TPS as a tumour marker for tumours such as hepatocellular carcinoma, breast cancer and prostate cancer is discussed, for example, in Wei-Jen Yao et al., Oncology 2001; 61:64-70; M. Sütterlin et al., Anticancer Research 17:2963-2966 (1997); J. M. Wolff et al., Anticancer Research 20:5003-5006 (2000).

In the papers by M. Sutterlin et al., Anticancer Research 17:2963-2966 (1997); B. Nisman et al., Cancer 1998; 82:1850-1859; and V. Stearns et al., Breast Cancer Research and Treatment 52:239-259, 1998, the suitability of TPS as a marker for organ-specific tumours is compared with other tumour markers, such as the further cytokeratin fragment markers CYFRA 8/18, CYFRA 21-1 and other classical tumour-associated antigens and CEA.

In septic patients, according to our knowledge, no systematic measurements of the soluble cytokeratin fragments, such as CYFRA 21-1 or TPS, have as yet been carried out. Nothing is as yet known about measured values of the cytokeratin fragments regarded as typical tumour markers in patients with systemic inflammations (sepsis), which measured values are significantly increased in the vast majority of cases.

A substantial increase in the concentrations of the soluble cytokeratin fragments CYFRA 21-1 and TPS and of the novel inflammation marker sCYFIF in the sera of the predominant number of sepsis patients was found, in addition to the findings of the model experiments with baboons presented in the prior Patent Application DE 101 30 985.6, for the first time in the investigations carried out by the Applicant and described in the following experimental reports with reference to four figures.

DETAILED DESCRIPTION OF THE INVENTION

Experimental Reports
1. Determination of CYFRA 21-1

The serum concentrations of the tumour marker CYFRA 21-1 were determined using a commercial assay (KRYPTOR-CYFRA 21-1 from B.R.A.H.M.S Diagnostica GmbH) in 169 sera of sepsis patients in whom high values for the sepsis marker procalcitonin (PCT) had been found. In 81% of the sepsis sera, increased CYFRA 21-1 concentrations (more than 1 ng/ml) were found. In the 50 sera used for the control, the CYFRA 21-1 concentrations exceeded the value of 1 ng/ml very slightly only in two cases.

Figure 1:
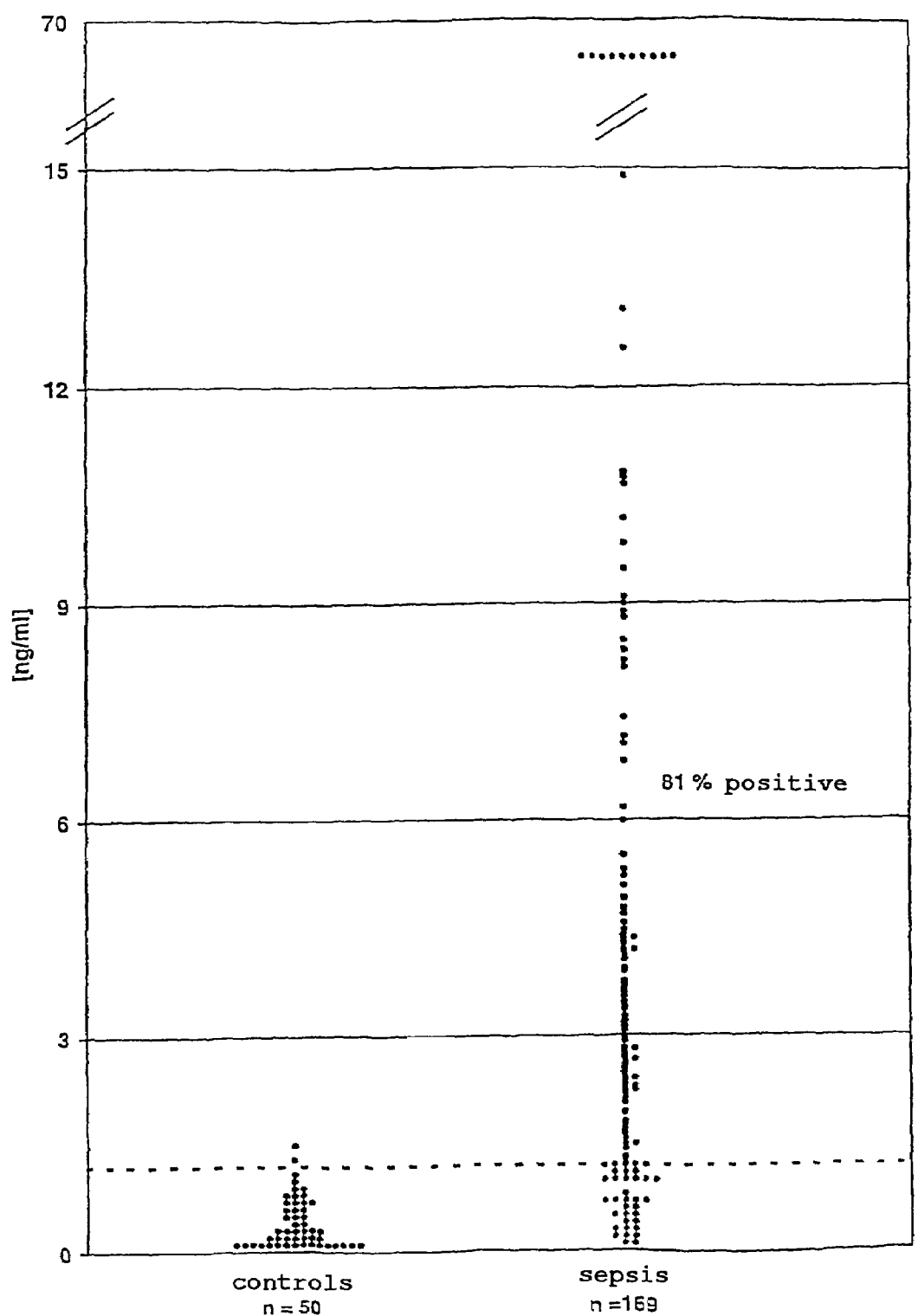
FIG. 1 shows the results of the determination of the parameter CYFRA 21-1 (a soluble cytokeratin-19 fragment) in the sera of 169 sepsis patients in comparison with a group of 50 control persons (blood donors)

A graph of the measured results is shown in FIG. 1.

Figure 2:
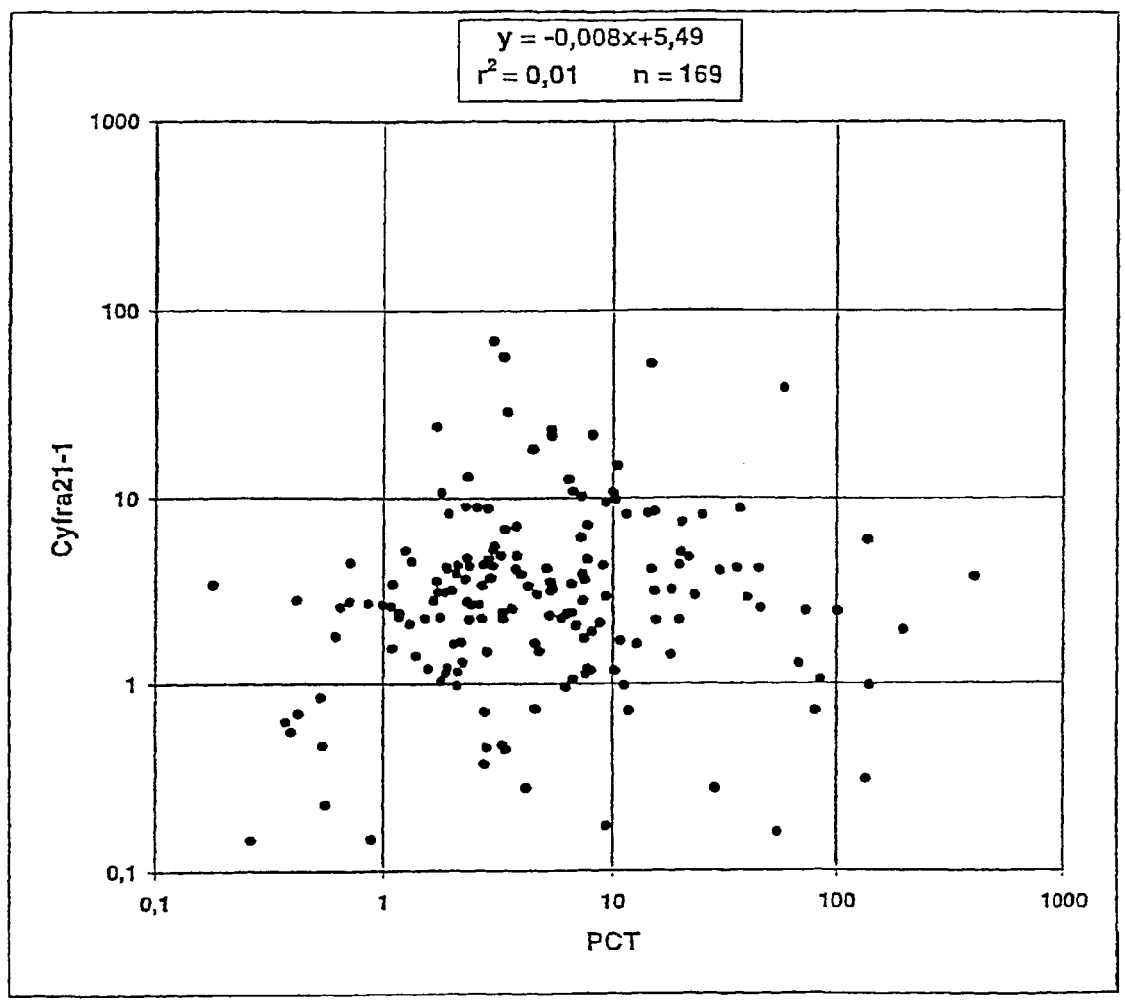
FIG. 2 shows the quantitative correlation of the results of CYFRA 21-1 determinations of the 169 sepsis patients of FIG. 1 with the results of the procalcitonin determination in the same sera.

If the CYFRA 21-1 values measured for individual sera are compared with the values measured for PCT, there is no positive quantitative correlation in the sense that the highest CYFRA 21-1 values are also found in sera in which the highest PCT concentrations were found. FIG. 2 shows the correlations found in the case of such a comparison. It is evident that high CYFRA 21-1 values (upper third of the graph) are also obtained at moderate PCT concentrations, and moderate values for CYFRA 21-1 at very high PCT concentrations (right third of the graph).

2. Determination of TPS

The serum concentrations of the tumour marker TPS were determined using a commercial assay for the determination of TPS (TPSTM from DPC-BIERMANN, Bad Nauheim) in 49 sera of sepsis patients in whom high values for the sepsis marker procalcitonin (PCT) had been found. In 90% of the sepsis sera, greatly increased TPS concentrations (more than 66 U/l) were found, while at the same time all 21 control sera (sera of healthy blood donors) were negative, i.e. had measured values below the reference value of 66 U/l.

Figure 3:
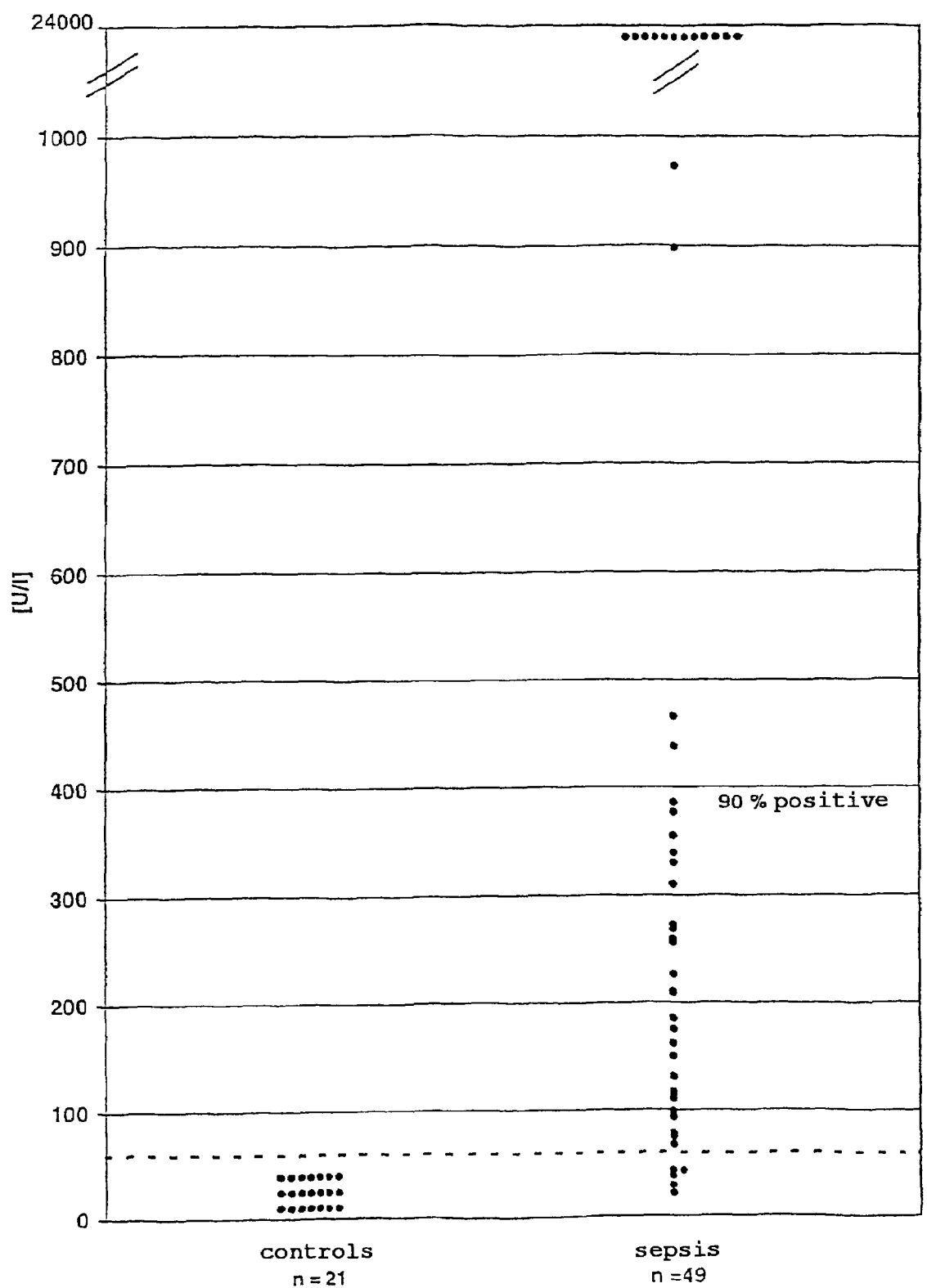
FIG. 3 shows the results of the determination of the parameter TPS (tissue polypeptide specific antigens; a soluble cytokeratin-18 fragment) in the sera of 49 sepsis patients in comparison with a group of 21 control persons (blood donors)

A graph of the results of the TPS measurement is shown in FIG. 3.

3. Determination of sCY1F

The serum concentrations of soluble cytokeratin-1 fragments sCY1F according to DE 101 30 985.6 were determined in 20 sera of sepsis patients in whom high values for the sepsis marker procalcitonin (PCT) had been found. In 95% of the sepsis sera, greatly increased sCY1F concentrations (more than 3 ng/ml) were found.

For the exploratory determinations of sCY1F in sepsis sera, a competitive luminescence immunoassay specially developed for this purpose was used, in which sheep antibodies against a peptide which comprised a partial sequence of the cytokeratin-1 fragment, that of the amino acids 214 to 229 of the SEQ ID NO:3 from DE 101 30 985.6, were used. The synthetic peptide used for obtaining the antibodies and as a competitor is commercially available under the name peptide PLY17 (Jerini BioTools GmbH). It has the amino acid sequence SEQ ID NO:1 shown in the sequence listing of the present Application.

The following procedure was adopted for carrying out the determinations of sCY1F:

Polystyrene tubes (from Greiner) were coated with 100 ng of peptide (PLY17; SEQ ID NO:1) in 300 μl of PBS. After incubation for 20 hours at room temperature, washing was carried out with 2×4 ml of PBS, containing 1% of BSA. The peptide-coated tubes were then used as the solid phase for carrying out the subsequent measurements, in which the immobilized peptides and the cytokeratin-1 fragments from the sample competed for a sheep antibody against the above-mentioned partial peptide sequence, which antibody was added in the form of an antiserum.

The following scheme was adopted for the measurement:
1. Pipette 100 pg of the sample (sepsis serum or control serum or calibrator solution) into the above-mentioned tubes;
2. pipette 200 μl of antiserum (diluted 1:5000 with PBS);
3. incubate for 2 h at room temperature while shaking;
4. wash the unbound antibody out of the tube (fill 4× with 1 ml of PBS and decant it);
5. add an acridinium ester-marked donkey anti-sheep antibody (B.R.A.H.M.S Diagnostica) in 300 ml of PBS, 1% BSA, for marking the solid phase-bound antibodies;
6. remove unbound marking antibodies after incubation for 2 h at room temperature, wash as under 4;
7. measure the acridinium ester bound to the solid phase, in a known manner by means of a luminometer (from Berthold).

For the preparation of a calibration curve, solutions containing known amounts of the synthetic peptide (SEQ ID NO:1) were used, and the concentrations of the cytokeratin-1 fragments were determined by comparison of the measured values for the sepsis sera with the calibration curve.

Figure 4:
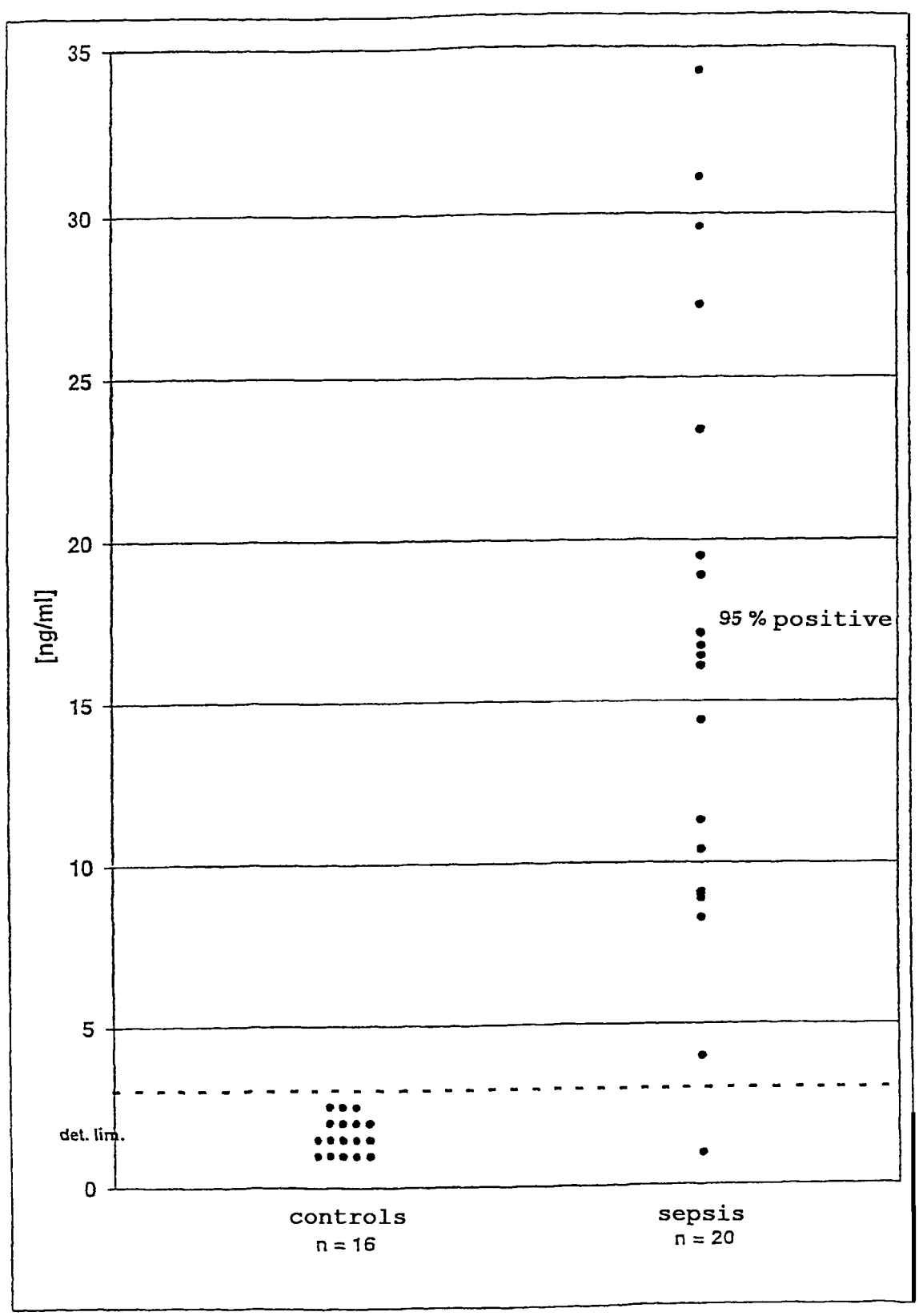
FIG. 4 shows the results of the determination of the parameter sCY1F (according to DE 101 30 985.6; a soluble cytokeratin-1 fragment) in the sera of 20 sepsis patients in comparison with a group of 16 control persons (blood donors).

A graph of the measured results is shown in FIG. 4. Very good sensitivity of the determination of the cytokeratin-1 fragments in sepsis is evident just by using the described provisional, very simple and insensitive competitive measuring procedure.

The substantial independence of the quantitative results of the determination of soluble cytokeratin fragments from those of the PCT determination shows that obviously different effects are measured in spite of the increased values for both parameters in the case of sepsis, which means that the measurement of both parameters provides more information than the measurement of only one of the parameters.

The combination of the determination of soluble cytokeratin fragments with that of one or more other sepsis markers is therefore a possibility for improving the fine diagnosis of sepsis and for improving the prognosis of the course of the disease and for therapy-accompanying monitoring in sepsis patients, it clearly being hoped that the interpretation of the results of such combined determinations based on the exact evaluation of individual cases documented as completely as possible (including, for example, information on the type of infection, reason for and course of the sepsis disease, characteristic data on age and sex of the patients) can be steadily improved with the number of cases evaluated.

The determination of soluble cytokeratin fragments can be carried out by any desired suitable detection method, but the determination in a patient's body fluid, especially in a serum, but also, for example, in the urine, by an immunodiagnostic method using suitable selective antibodies appears to be the most advantageous from practical points of view. Commercial assays for the determination of some soluble cytokeratin fragments are already available and can also be used in the context of the present invention. If necessary, good accuracy of measurement in the measuring range relevant for sepsis diagnosis should be ensured.

Thus, the determination of soluble cytokeratin fragments can be carried out for sepsis diagnosis, and in particular for early differential diagnosis and for detection and for the preparation of a prognosis, for assessment of the severity and for therapy-accompanying assessment of the course of sepsis, in particular by determining the content of soluble cytokeratin fragments in such a method in a sample of biological fluid of a patient and drawing conclusions about the presence of a sepsis from the established presence and/or amount of soluble cytokeratin fragments and correlating the result obtained with the severity, the progress of the sepsis and/or the tissue or organ most strongly affected by the sepsis and appropriately choosing the possible treatments and/or estimating the treatment prospects.

The invention claimed is:

1. A method for diagnosis and detection of sepsis, comprising providing a biological fluid of a patient in whom sepsis is suspected based on clinical findings and elevated levels of procalcitonin in said patient; and determining the amount of cytokeratin fragment 21-1 (CYFRA 21-1) in said fluid wherein an elevated concentration of CYFRA 21-1 in said fluid as compared to healthy individuals is indicative of sepsis.

2. The method of claim 1, wherein the amount of CYFRA 21-1 is determined by an immunodiagnostic assay method.

3. The method of claim 1, wherein said biological fluid is patient's serum.

4. The method of claim 1, wherein CYFRA 21-1 in an amount greater than 1 ng/ml is indicative of sepsis.

* * * * *